United States Patent
Wieringa et al.

(10) Patent No.: US 8,630,465 B2
(45) Date of Patent: Jan. 14, 2014

(54) IMAGING OF BURIED STRUCTURES

(75) Inventors: Fokko Pieter Wieringa, Elst (NL); Dirkjan Bakker, Alphen aan den Rijn (NL); Antonius Franciscus Wilhelmus van der Steen, Rotterdam (NL); Frits Mastik, Rotterdam (NL); Rene Gerardus Maria van Melick, Marken (NL)

(73) Assignee: Nederlandse Organisatie voor toegepast-natuurwetenschappelijk onderzoek TNO, Delft (NL)

( * ) Notice: Subject to any disclaimer, the term of this patent is extended or adjusted under 35 U.S.C. 154(b) by 1132 days.

(21) Appl. No.: 10/598,077

(22) PCT Filed: Feb. 15, 2005

(86) PCT No.: PCT/NL2005/000108
§ 371 (c)(1),
(2), (4) Date: Nov. 19, 2007

(87) PCT Pub. No.: WO2005/079662
PCT Pub. Date: Sep. 1, 2005

(65) Prior Publication Data
US 2009/0028461 A1    Jan. 29, 2009

(30) Foreign Application Priority Data
Feb. 19, 2004 (EP) .................................. 04075541

(51) Int. Cl.
*G06K 9/00* (2006.01)
(52) U.S. Cl.
USPC .......................... 382/128; 382/154; 382/284
(58) Field of Classification Search
USPC ....................................................... 382/128
See application file for complete search history.

(56) References Cited

U.S. PATENT DOCUMENTS

| 4,555,179 | A | * | 11/1985 | Langerholc et al. | 356/342 |
| 5,137,355 | A | * | 8/1992 | Barbour et al. | 356/342 |
| 5,699,797 | A | | 12/1997 | Godik | |
| 2001/0027273 | A1 | | 10/2001 | Flock et al. | |
| 2002/0181762 | A1 | * | 12/2002 | Silber | 382/154 |
| 2005/0036667 | A1 | * | 2/2005 | So et al. | 382/128 |

FOREIGN PATENT DOCUMENTS

WO    WO 01/15597  A1    3/2001

OTHER PUBLICATIONS

International Search Report from PCT/NL2005/000108 (May 6, 2005).

* cited by examiner

*Primary Examiner* — Phillip A Johnston
(74) *Attorney, Agent, or Firm* — Leydig, Voit & Mayer, Ltd.

(57) ABSTRACT

A method of obtaining an image of buried structures in an object, comprising: providing a camera for imaging visual and infrared-images; providing a bounded light source; partly irradiating said object by said bounded light source; imaging a non-irradiated area of said object by said camera to image said buried structure; and combining said buried structure image with a visual image of said object. Accordingly an image can be obtained while discarding specular reflections of the object. Additionally there is disclosed a method of enhancing imaging of buried structures in an object, comprising: aligning said infrared light source with a visual light source; providing a first edge analysis of said infrared image; providing a second edge analysis of said visual image; comparing said first and second edge analysis; and discarding edges in said infrared image that are also detected in said second image.

13 Claims, 10 Drawing Sheets

Device viewed from the irradiated tissue side

A

B

C

IMAGING OF BURIED STRUCTURES

FIELD OF THE INVENTION

Background

The invention relates to a method of obtaining an image of buried structures in an object, in particular to imaging structures such as vascular structures in biological tissue by means of selective combining information derived from tissue images in the visible range and the infra-red range.

A method describing such is disclosed in the international application WO0115597 by the same inventor. It has been found, that obtaining a sufficiently clear image is difficult due to various problems. One problem is, that light emanating from buried, in particular deeper parts of the object is often much weaker than the light that is reflected directly by the surface of the object. In practice, this means that a separation of the specularly reflected light and light emerging from deeper parts of the object may be needed in order to identify underlying structures.

While separating these two types of light, for instance by a known method of using polarized light and using the fact that specularly reflected light keeps its polarization direction, so that it can be filtered out by means of a polarizing filter, a substantial amount of the light is lost that is originating from the lower parts of the object, thus resulting in a loss of image brightness and resolution. This invites to the use of powerful light sources in order to receive sufficient light from the lower parts in the process of separating the two parts. However, especially in the area of imaging structures in live objects, there is a maximum amount of light that may be irradiated on the object.

WO01/50955 shows a reflective arrangement where specular light is filtered by a polarizator. The image of an underlying structure is combined with a visual image to present a single image. However, it has been found that straightforward combination of these images offers problems, in particular, since certain artefacts occur that are inconvenient to reliably detect and locate an underlying structure.

US2001/0037811 shows a probe for determining a circumference of a finger. Additionally, the joint is transilluminated for inspecting arthritis inflammation from a scattering analysis. This arrangement cannot be used for visually imaging body parts with a freedom comparable to the human eye.

SUMMARY OF THE INVENTION

The invention has as an object to provide an imaging technique that does not suffer from the afore described problems and that is able to provide an enhanced image of the underlying structure. Moreover, the invention has as an object to provide an imaging enhancement technique to enable a person to combine visual information and information of buried objects in one image.

To achieve these and other goals, in one aspect, the invention offers a method according to the features of claim 1. In another aspect, the invention offers a method according to the features of claim 14.

In particular, by providing a camera for imaging visual and infrared-images; providing a bounded light source for partly irradiating said object by infrared light; partly irradiating said object by said bounded light source; imaging a non-irradiated area of said object by said camera to image said buried structure; and combining said buried structure image with a visual image of said object, infrared light incident on the image that is originating from a direct reflection is spatially filtered out of the image. The remaining partial image hence does not suffer from saturation effects due to direct illumination of specularly reflected light. In a preferred embodiment, a full image is provided by varying said partial irradiation in time so as to provide a full image by subsequent combining of said partial images.

In a further preferred embodiment, said partial image is obtained by scanning a light beam over said object. In addition or alternatively, said partial image is obtained by subsequently irradiating said object by predetermined patterns. One particularly preferred embodiment comprises obtaining said partial image by alternatingly irradiating said object by a predetermined complementary patterns. For instance, in an embodiment said patterns may be matrix-patterns, line patterns, dot patterns, concentric or circular patterns.

Further, preferably said object is irradiated only at predetermined positions that are spaced apart. By spacing the irradiation area and the light detection area, deeper parts of the buried structure may be enhanced.

By alternatively illuminating said object, a full image may be provided, and wherein all areas of the object are irradiated in a time-dependent manner.

The invention further offers particular benefits while using a CMOS-camera, since these camera's have a high degree of decorrelation of adjacent pixels. Thus, the effect of "blooming" is prevented, so that there is a high contrast between the directly reflected area (that is discarded) and the remaining area which receives diffuse light originating from deeper layers.

Furthermore, the invention is preferably used while aligning said infrared light source with a visual light source; providing a first edge analysis of said infrared image; providing a second edge analysis of said visual image; comparing said first and second edge analysis; and discarding edges in said infrared image that are also detected in said second image. This offers the benefit of obtaining a "normal" visual image (as seen by the human eye), that is enhanced by identifying the underlying structure (detected using infrared light) within the visual image while discarding false edges formed by shadowing or aliasing artifacts (e.g. shadows or reflections from a scalpel or needle). For instance, for surgical purposes, the method offers a convenient tool for deciding an optimal entry point in the object, for instance for cutting tissue or the like.

Preferably, said edge-detection is performed by a gradient analysis of said first image. The invention offers a convenient embodiment when said images are provided stereoscopically. Furthermore, said first image may be spectrally analysed, and wherein said spectral analysis is projected into said second image. Furthermore, said spectral analysis may comprise a pulsatility analysis and/or a hart beat frequency analysis and/or respiratory frequency analysis. Such analysis thus offers a convenient non-contact tool for measuring body parameters of interest. Under "pulsatility analysis" is understood at least a determination of pulsating parts in the object of interest.

The invention is further related to a method of enhancing imaging of buried structures in an object, comprising: as defined in claim 14. Furthermore, the invention is related to a system as defined in claim 16.

BRIEF DESCRIPTION OF THE DRAWINGS

Further features and benefits will become apparent from the figures. In the figures.

DETAILED DESCRIPTION OF THE DRAWINGS

Figure 1:
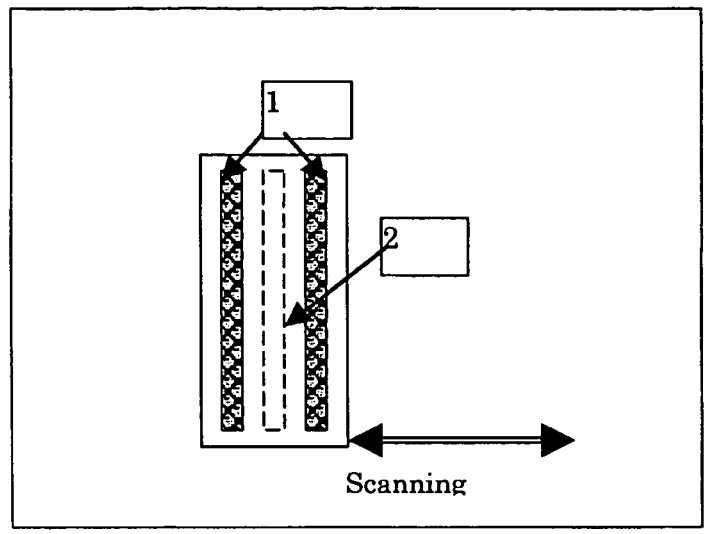
FIG. 1 shows a schematic view of a scanning irradiating method of an object according to the invention.

FIG. 1 shows an alternative to the above described polarization filtering method. This method comprises dynamic complementary lighting/scanning of alternating patterned image sections. This method does not require the use of polarization filters. It is based on the fact that photons entering biological tissue will strongly scatter within the tissue which partly results in backscattering.

Furthermore the viewed area is divided into parallel linear areas, which we will call "line sections". These line sections can be divided into even and uneven line sections 1, 2 respectively.

Using a camera that has good anti-blooming specifications and allows the read-out of freely selectable rectangular pixel regions we then can acquire image information in a special sequence.

During a certain period the bounded light source will light all even line sections 1 and the camera will acquire image information from all uneven line sections 2. Here, the term bounded encompasses light that is bounded spatially, so that an illuminated object comprises, in a direction of view which is also a direction of illumination, non-illuminated areas which are not reached by the bounded light source. Such bounding can be typically reached by focusing, collimating or shielding the light source. Also various other light sources, such as laser lights (e.g. in combination with a holographic grating) and LEDs, can produce bounded lights. During the next period the uneven line sections 2 are lighted and the camera will acquire image information from the even line sections. This can either be done with a line camera that scans the entire tissue or with a normal camera that scans all even lines simultaneously and during the next period all uneven lines.

Figure 2:
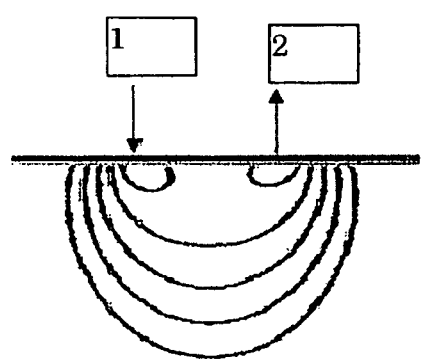
FIG. 2 shows a schematic view of foton-migration in live tissue due to diffusion.

In FIG. 2 is illustrated how light diffused within the tissue can be used to image deeper parts of the object. Light enters the object at one position 1 and leaves the object at another position 2. From the figure it becomes clear that light entering at further distanced positions can collect information from parts deeper within the object. By applying a variety of illumination patterns as will be further described with reference to FIG. 3-FIG. 5, illumination from "within" the object can be achieved, thus imaging deeper parts of the object.

Figure 3:
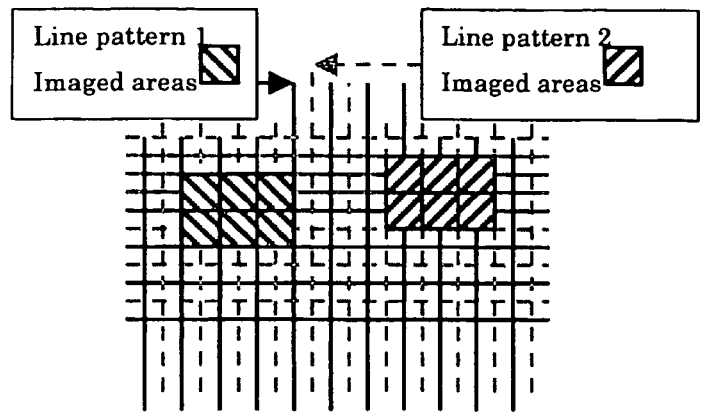
FIG. 3 shows an illumination method by illuminating an overlapping pattern on the object.
Figure 4:
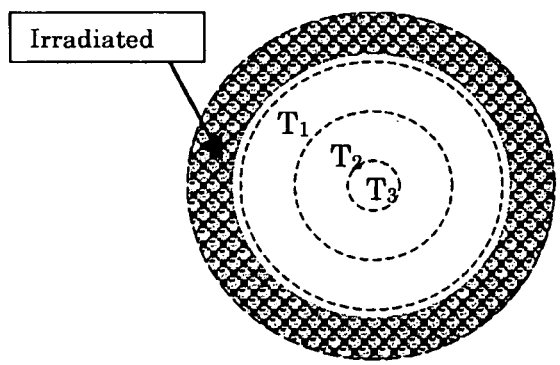
FIG. 4 shows an illumination method by illuminating a circular patterns on the object.

To this end, in FIG. 3, instead of even and uneven parallel lines shown in FIG. 1, alternate spatially shifted crossed line patterns can be used as lighting pattern whilst image acquisition occurs within the areas between the lines. It is also possible to first project an "even" dot pattern on the cross point of line pattern 1 and then project an "uneven dot pattern on the cross sections of line pattern 2. Also, in FIG. 4 discrete concentric circular areas can be used. Satisfying results were obtained by a simple test of circular irradiation geometry disclosed in FIG. 4. A 6 mm thick slice of pink foam (3M ethafoam) was laid upon the shielding pipe. On top of this foam slice a plastic office clamp was placed, with its' white plastic paper retaining slice laying across it. Finally a second slice of pink foam was laid on top. Outside the camera's field of view, a ring light injected photons of 660 nm, 810 nm and 940 nm into the foam, perpendicular to the foam surface.

Figure 5:
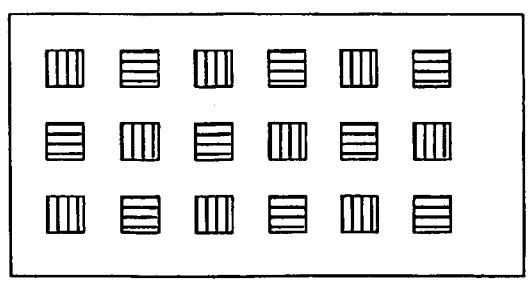
FIG. 5 shows an illumination method by illuminating a grid of patterns on the object.

FIG. 5 shows another embodiment, wherein said object is irradiated only at predetermined positions that are spaced apart. First areas 3 indicated with horizontal lines are irradiated in a first period; second areas 4 with vertical lines are irradiated in a second period. Such a spaced apart configuration is able to show deeper parts of the structure. By varying the spacing, lower and deeper parts of the object may be scanned.

Figure 6:
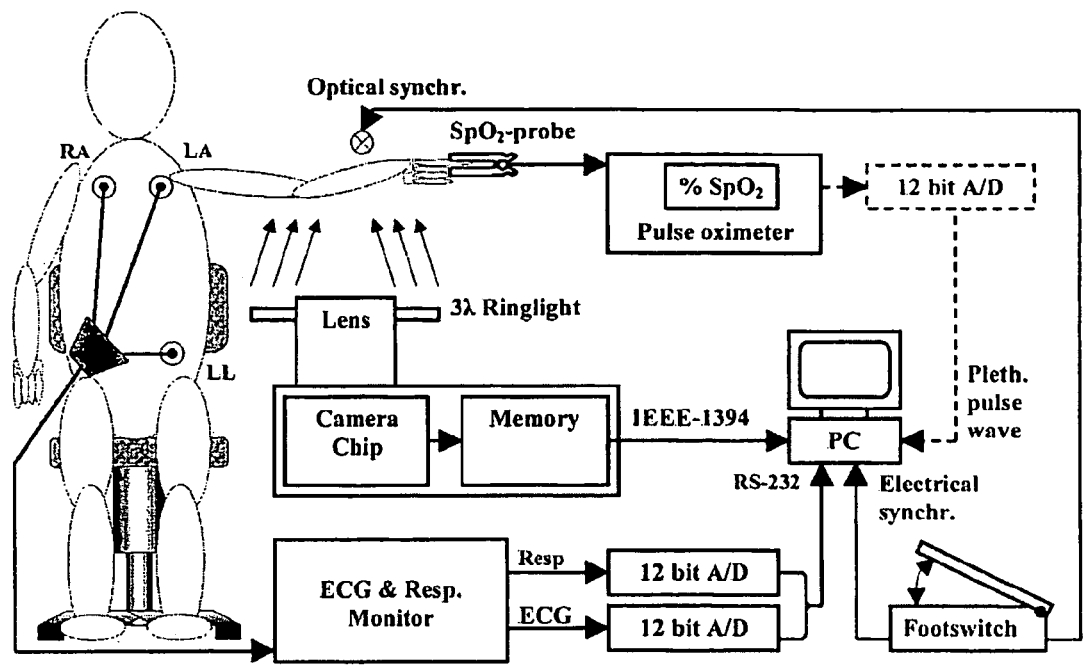
FIG. 6 shows a testing arrangement for testing the apparatus according to the invention using one visible wavelength and two infrared wavelengths.
Figure 7:
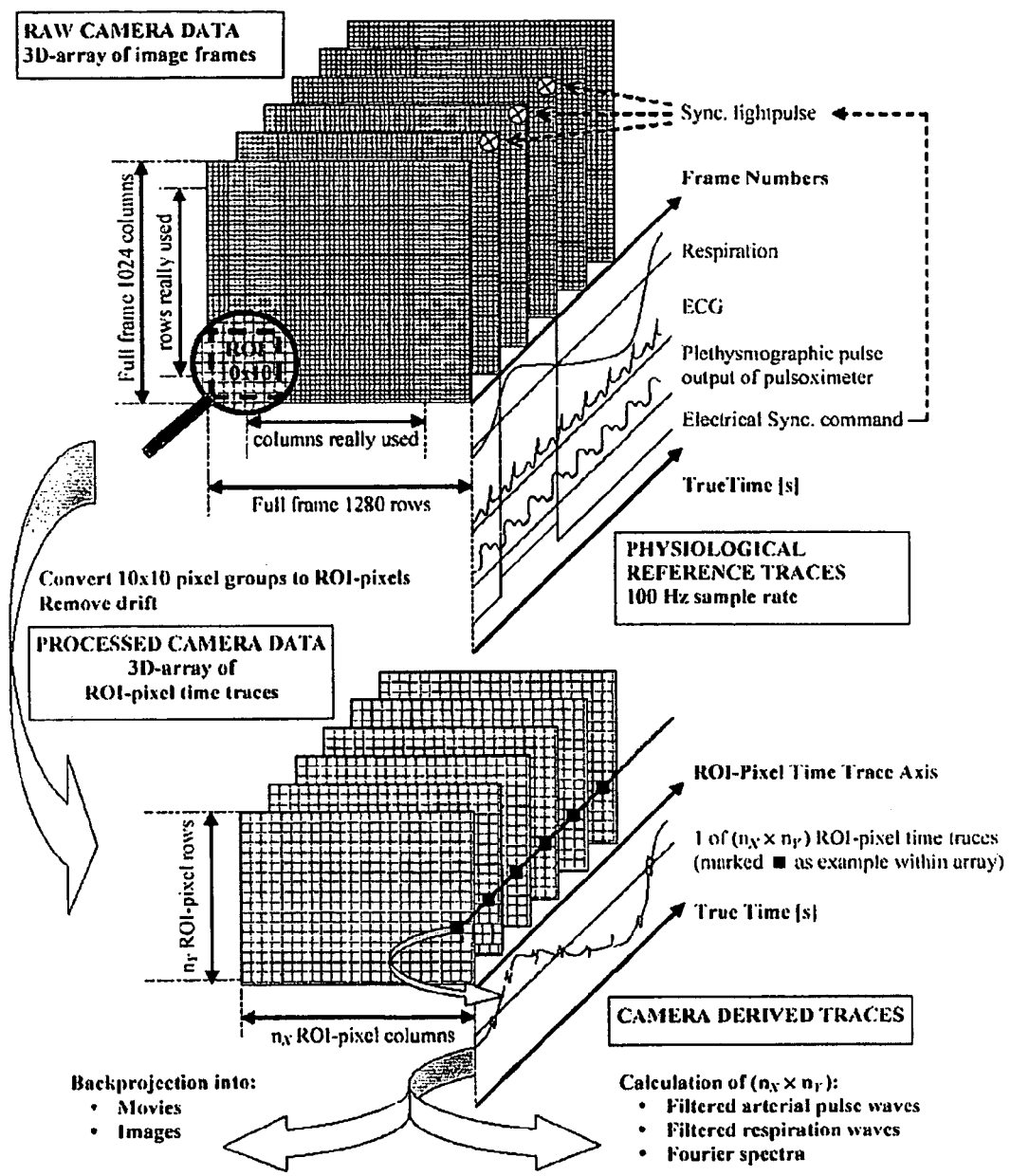
FIG. 7 shows a series of analysis steps for processing and routing of data acquired from the arrangement of FIG. 6.
Figure 8:
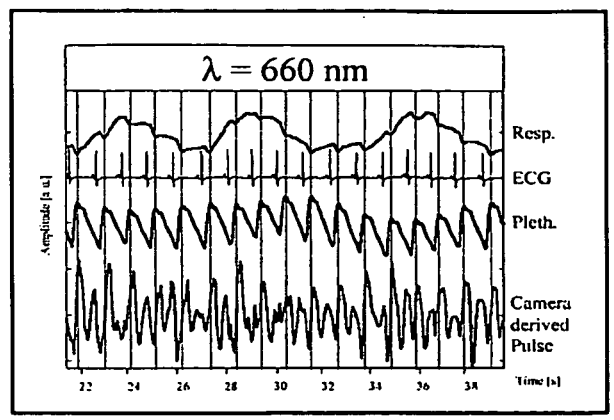
FIG. 8 shows a spectral analysis of the pulsatile components in said image for light of three different wavelengths.
Figure 8:
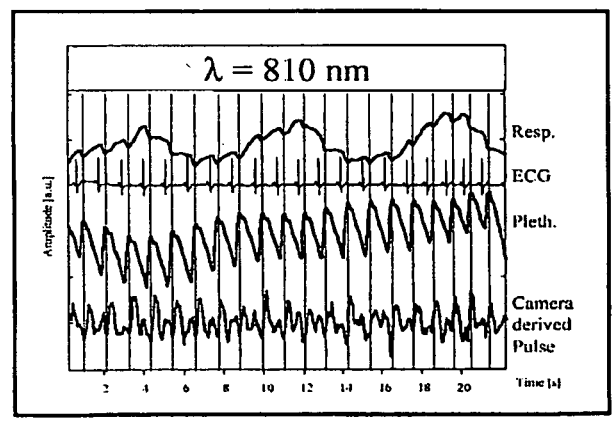
Figure 8:
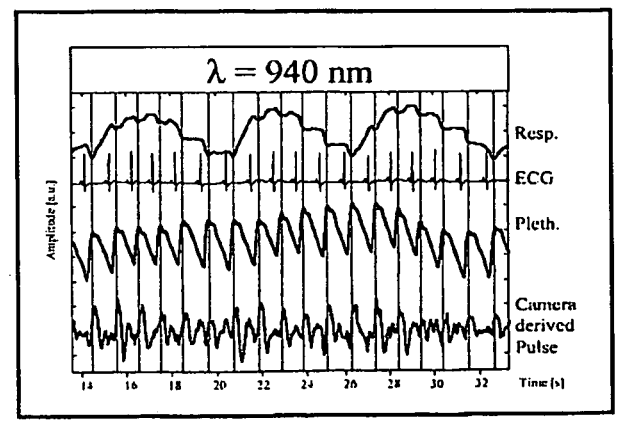

FIG. 6 shows a testing arrangement, where an embodiment of the inventive method was tested using known markers such as an SPO2 pulse oximeter, an ECG recording devise and a respiratory frequency monitor. The signals were recorded and sampled using the steps indicated in FIG. 7. This leads to a pixel by pixel time-analysis of intensity variation. The frames were sampled at a 100 Hz Sample rate and the recorded respiration, ECG and plethismographic pulse output were compared. The outcome is illustrated for a variety of wavelengths in FIG. 8. It is clearly shown how well the measured variation of the camera matches with the other pulse signals.

A special configuration with added value is based upon two cameras (e.g. CCD or CMOS monochromatic or multiband) positioned at a certain distance from each other (e.g. eye-to-eye distance) thus stereoscopically viewing the same object (e.g. biological tissue), a dual channel electronic image processing device and two display devices placed in front of both eyes.

Between each camera and the viewed object an additional optical system (maybe combining 2 channels) may be placed (e.g., a dual channel microscope, endoscope, colposcope, etc.) It is possible to incorporate a simple vizor-like construction 5 (see FIG. 9) so that the device can be either put in front of the eye or be positioned out of the viewing angle to allow normal sight.

Figure 9:
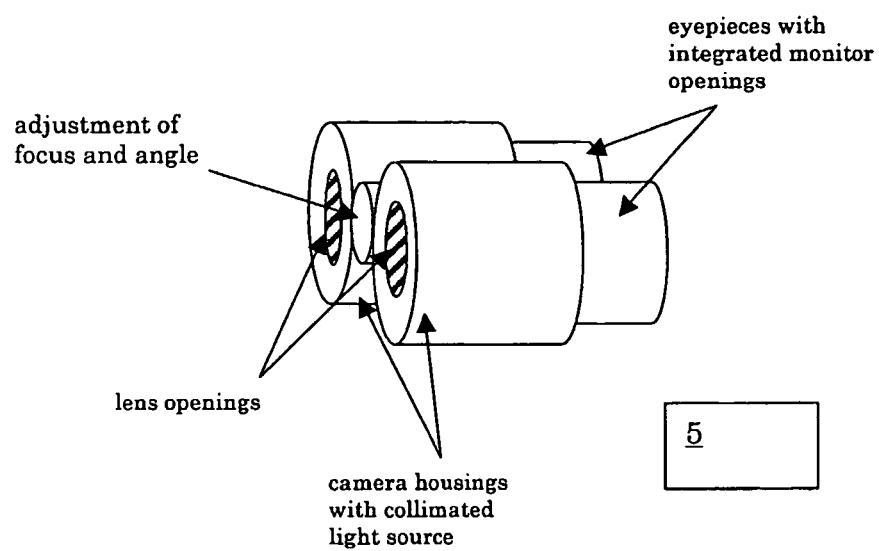
FIG. 9 shows a simple vizor-like construction comprising the apparatus of the invention.
Figure 10:
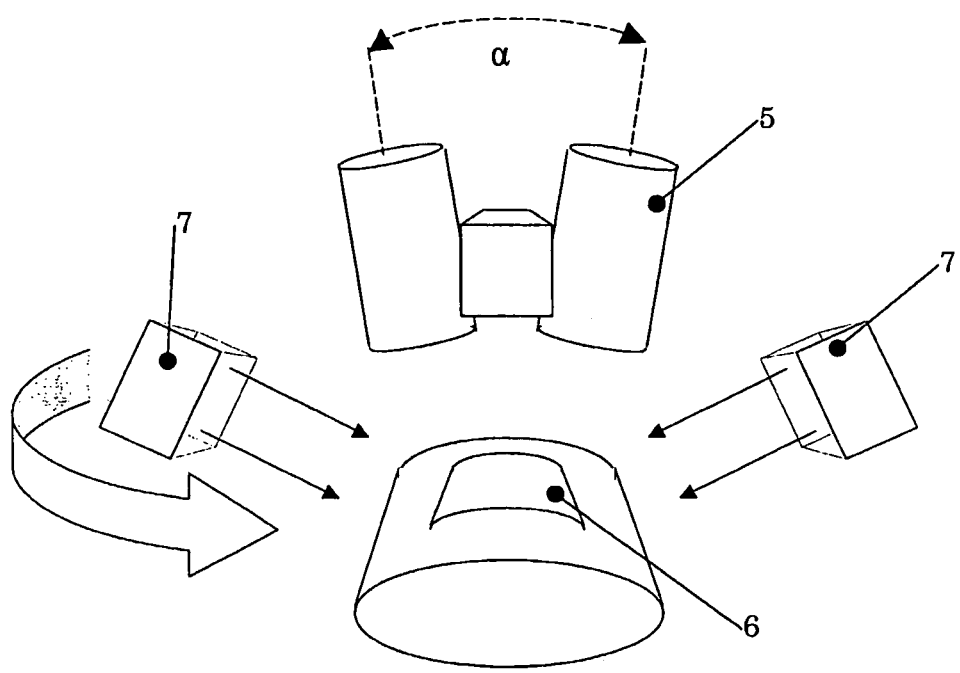
FIG. 10 shows the vizor-like construction of FIG. 9 in use.

FIG. 10 shows as an example the stereoscopic eyepiece 5 of FIG. 9 in use. For the eyepiece, a color camera can be applied with a bayer color filter pattern of which all filter colors are highly transparent in the NIR-range. Also a multi-layered camera chip (Patent WO 02/27804 to Foveon Inc. or earlier patents like U.S. Pat. No. 4,238,760 to Carr) or the approach in our previous patent WO 01 15597 A1 can be applied. Preferably, the images in both spectral ranges match pixel to pixel.

The surface of the viewed biological tissue region 6 is irradiated at an oblique angle from two opposite sides by two light sources 7. These two sides need not to be aligned with the Left/Right axis of the eyepiece 5, but can be swiveled around in a plane perpendicular to the central axis of the joined cameras.

The light sources 7 can be controlled to independently send out broadband white light in the visible wavelength range (VIS; 400-780 nm) or narrowband light in the near infrared range (NIR; e.g. 920 nm) as well as in both ranges (VIS & NIR). The light sources 7 are carefully constructed so that the geometrical beam profiles of VIS and NIR are aligned resulting in identical shadowing in the VIS and NIR images. As an alternative also a surgical stereo microscope or an endoscopic dual channel camera (as used in stereoscopic robot surgery) with two side fiber light guides can be used to collect the images.

Figure 11:
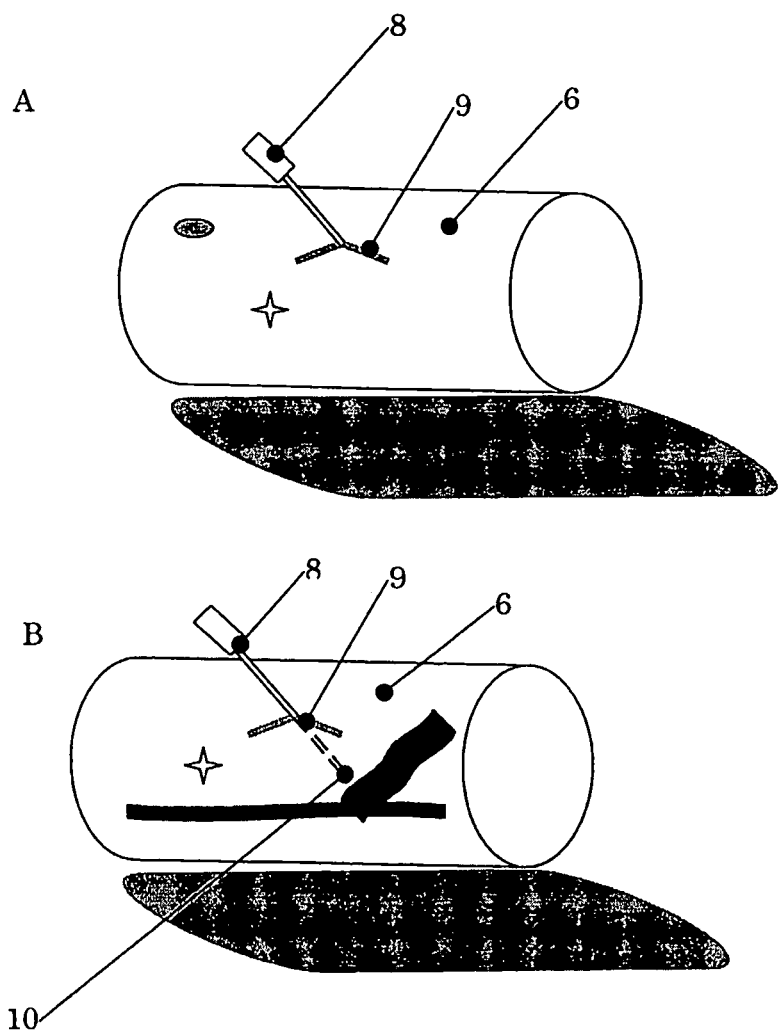
FIG. 11 shows the VIS and NIR images collected by the eyepiece of FIG. 9.
Figure 12:
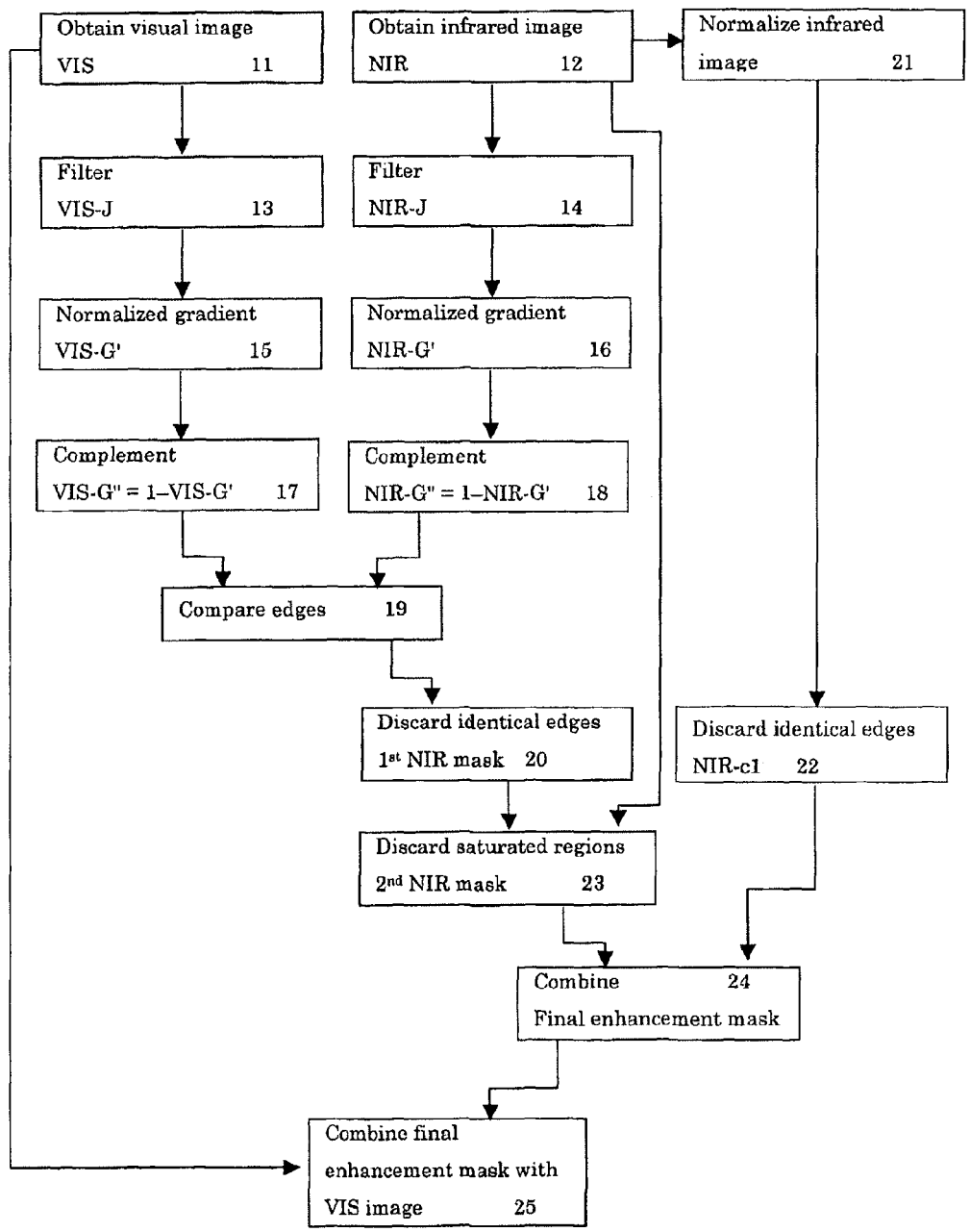
FIG. 12 illustrates the steps according to the method of the invention.

FIG. 11 shows the result of the VIS (FIG. 11 A) and NIR (FIG. 11 B) images such as collected by the eyepiece 5 illustrated in FIG. 10. Since NIR and VIS beams are matched, shadows produced by irregular shapes at the tissue surface (e.g. skin structure, skin folds, molds, etc.) will also match in both wavelength ranges. In the embodiment disclosed, the beams are oriented at a small angle with respect to the tissue region 6. As a result, skin folds etc. will produce sharp-edged shadows. Shiny areas that produce reflections and/or saturated pixels (marked as a star) will also match in both wavelength ranges. Due to the small angle, objects 8 that are brought towards the tissue surface 6 (e.g. needles, scalpels, probes, etc.) will produce two separate shadows. These shadows will meet and typically form a "V" pattern 9 when an object touches the surface. If e.g. a needle punctures the surface, then the needle tip 10 will quickly disappear from the VIS image (FIG. 11 A). On the NIR image (FIG. 11 B) however, the tip 10 will remain visible within the tissue 6 (see figure).

On the VIS image (FIG. 11 A), only very superficial blood vessels will be visible, especially if the texture of the vessel deforms the skin. On the NIR image, however, blood vessels will be visible much better (even blood vessels at a depth of a few millimeters below the surface). Since skin pigment (melanin) has a very low absorbance within the NIR region this good NIR visibility will also be the case with dark skinned persons (also molds will lose their dark color).

After obtaining the NIR and VIS images in steps 11 and 12 respectively, a gradient edge enhancement step is applied for both spectral bands as will be illustrated with reference to FIG. 16 (steps 13 and 14). Image VIS-J and NIR-J are obtained by filtering with a smoothing filter to suppress noise from camera image NIR and VIS. In the current implementation this is an averaging filter. From each smoothed images VIS-J and NIR-J, two directional difference images Ix and Iy are calculated by means of a gradient filter. Currently this it performed with a Prewitt filter.

Next edge gradient images VIS-G and NIR-G are made by $\sqrt{(Ix^2+Iy^2)}$. Then VIS-G and NIR-G are clipped and normalized to 1 to obtain VIS-G' and NIR-G' (Steps 15 and 16). Finally the images are complemented to 1-G' (Steps 17 and 18).

For a given tissue region a VIS image and a pixel to pixel matching NIR image are acquired.

The images from both spectral bands are subjected to an identical edge enhancement algorithm (see above), producing normalized NIR-edge and VIS-edge grayscale images so that edges are encoded black (0=black and 1=white; note that this is the negative of normal edge enhanced results).

Now corresponding edges in the NIR and VIS image are determined (Step 19) according to a pixel by pixel criterion:
NIR-edge-pixel<NIR_Treshold AND VIS-edge-pixel<VIS_Treshold (Thresholds are both software configurable)

By combining information from both spectral regions, the pixel coordinates that match both requirements are identified as superficial artifacts and are discarded by setting the pixel value to 1 in the corrected NIR edge image (Step 20).

By doing the same in the raw NIR image after normalizing (Step 21) (no edge enhancement) a corrected normalized NIR image (Step 22) is defined by discarding saturated image areas.

To this end, the locations of all saturated pixels within the raw NIR image (e.g. 256 for an 8-bit image) are identified. For all pixels within the 1st NIR-mask that are saturated or a direct neighbors of a saturated pixel, the edges are discarded by setting the pixel value to 1 (and thus completely ignoring edge information) is filled in, resulting in a second NIR-mask (step 23).

False edges resulting from saturated pixels are thus removed and the 2nd NIR-mask now contains the boundaries of subcutaneous blood vessels (and eventual other buried contrasting structures).

This approach can be varied by including second, third etc. neighboring pixels.

In a preferred mode, the raw IR image is used to provide "filled in" blood vessels; for example, by multiplying the 2nd NIR-mask with the 2nd corrected NIR image (step 24). The amount of fill-in colorization can be varied with a user adjustable exponent N:

$$\text{2nd NIR-mask} \times (\text{1st corrected NIR image})^N = \text{final enhancement mask}$$

Finally, this final enhancement mask now is multiplied with the luminosity component of the raw VIS image (which preferably is a color image) in step 25. In this way only contrast information that truly originates from below the tissue surface is projected into the VIS image. If we look at the previous drawings with a needle inserted in tissue it is clear that these criteria will lead to superimposing only the buried needle tip upon the VIS image. Shadows, wrinkles, reflections and the edges of molds will not be enhanced.

The detection of purely superficial artifacts thus can be further improved when instead of taking all colors of the visible region into account, only the Blue spectral range is used for the VIS edge enhancement input. This is done in order to suppress the visibility of blood vessels. This effect of blue light is because in the visible range, the reflectivity of vessels for blue light is the nearest to skin (the maximum visible vessel contrast lies outside the blue range). As another optional refinement the final enhancement mask may be selectively multiplied with e.g. only the Red and/or Green portion of the visible image (instead of the luminosity signal of the total visible color image).

When an interesting tissue portion is spotted, the user can switch to a mode that alters the image capturing sequence and allows the collection of an additional (second) NIR image within a selected region of interest (ROI). This ROI is virtually illuminated by photon injection just outside the ROI by means of EITHER a LED-array in contact with the tissue OR a pattern of laser dots or laser lines projected onto the tissue from a distance. During acquisition of this second NIR image the VIS and first NIR lighting are off.

In this way information obtained using two types of lighting geometries for the same wavelength range can be combined. This can be done with or without also using VIS and flashing needle tip lighting as will be illustrated with reference to FIG. 13.

Figure 13:
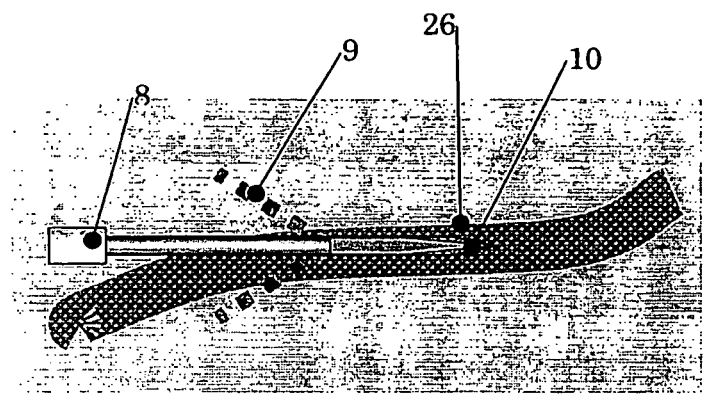
FIG. 13 shows a further embodiment of the inventive system including an infrared emitting puncture tool.
Figure 13:
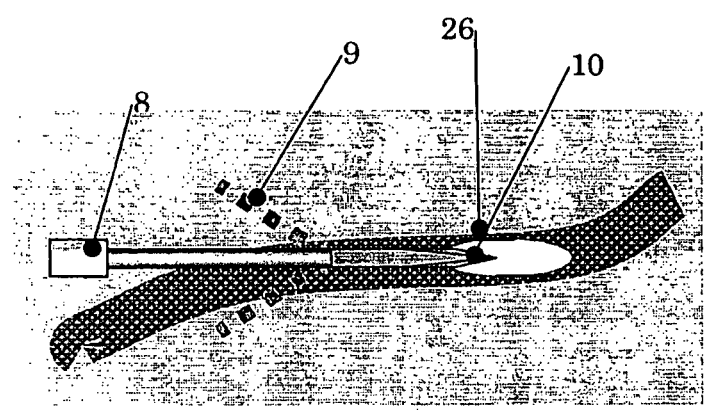
Figure 13:
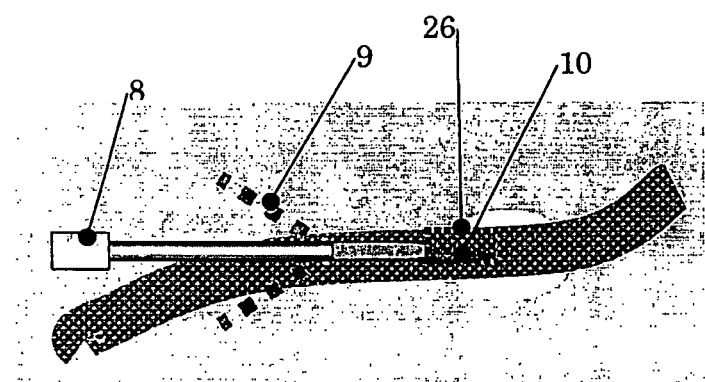

In FIG. 13 a NIR-laser or NIR-LED is plugged onto a needle or catheter 8. Via a sterile window light is projected through or alongside the needle bore. In this way the needle tip 10 illuminates the vessel interior wall 26 when the needle is in the vessel (see FIG. 13B). If the needle punctures the distal vessel wall (see FIG. 13C) a drastic change in illumination is seen. The light source clipped to the needle may be synchronized with the cameras. A flashing tip illumination may be beneficial.

Although in the preceding the invention has been further illustrated with reference to the drawings and the description it will be clear that the invention is not limited thereto and that these embodiments are only disclosed for the purpose of illustration. Variations and modifications thereto are within the scope of the invention as defined in the annexed claims.

The invention claimed is:

1. A method of obtaining an image of a buried structure in an object comprising:
   providing a camera for imaging visual and infrared-images;
   providing a bounded infrared light source;
   partly irradiating said object by said bounded infrared light source;
   imaging an area of said object, by said camera, that is not irradiated by said bounded infrared light source to create an infrared image of said buried structure from infrared light scattered off the buried structure and tissue surrounding the buried structure;
   combining said image of said buried structure with a visual image of said object;
   aligning said bounded infrared light source with a visual light source;
   providing a first edge analysis of the infrared image;
   providing a second edge analysis of the visual image;
   comparing a first set of edges detected during said first edge analysis with a second set of edges detected during the second edge analysis; and
   discarding, based on the comparing the first set and second set of images, edges detected in the infrared image that are also detected in the visual image.

2. A method according to claim 1 wherein irradiation of said object, during the partly irradiating step, is varied in location over time so as to provide a full image by subsequently combining partial images rendered during multiple iterations of the imaging step.

3. A method according to claim 1, wherein said image of said buried structure is obtained by scanning a light beam over said object.

4. A method according to claim 1, wherein said image of said buried structure is obtained by subsequently irradiating said object in predetermined patterns.

5. A method according to claim 4, wherein said predetermined patterns are complementary patterns.

6. A method according to claim 4, wherein said predetermined patterns comprise any one or more of the group consisting of: matrix-patterns, line patterns, dot patterns and concentric patterns.

7. A method according to claim 4, wherein said object is partly irradiated only at predetermined positions that are spaced apart.

8. A method according to claim 1, wherein said camera is a CMOS-camera.

9. A method according to claim 1 further comprising the step of correcting said infrared image to discard saturated image areas.

10. A method according to claim 1, wherein said image of said buried structure and visual image are provided stereoscopically.

11. A method according to claim 1, wherein said infrared image is spectrally analyzed, and wherein said spectral analysis is projected into said visual image.

12. A method according to claim 11, wherein said spectral analysis comprises a pulsatility analysis and/or a heart beat frequency analysis and/or respiratory frequency analysis.

13. A system for obtaining an image of a buried structure in an object, comprising:
   a bounded infrared light source, the light source aligned with a visual light source, for partly irradiating said object by light;
   a camera device arranged for imaging an area of said object that is not irradiated by said bounded infrared light source for obtaining an infrared image of said buried structure from infrared light scattered off the buried structure and tissue surrounding the buried structure, and for obtaining a visual image of said object; and
   a processing device arranged for:
      providing a gradient analysis of said infrared image to detect edges of said buried structure;
      providing a gradient analysis to detect edges in said visual image;
      comparing edges detected during the gradient analysis of said visual image with edges detected during the gradient analysis of said infrared image;
      discarding edges detected in said infrared image that are also present in the edges detected in said visual image to render a modified infrared image; and
      combining said modified infrared image and visual image to depict edges of said buried structure in said second visual image.

* * * * *

UNITED STATES PATENT AND TRADEMARK OFFICE
CERTIFICATE OF CORRECTION

PATENT NO. : 8,630,465 B2
APPLICATION NO. : 10/598077
DATED : January 14, 2014
INVENTOR(S) : Wieringa et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1706 days.

Signed and Sealed this
Twenty-second Day of September, 2015

Michelle K. Lee
*Director of the United States Patent and Trademark Office*